United States Patent
Liu et al.

(10) Patent No.: US 10,758,702 B2
(45) Date of Patent: Sep. 1, 2020

(54) HUMIDIFICATION DEVICE, HUMIDIFIER AND VENTILATOR

(71) Applicant: BMC MEDICAL CO., LTD., Beijing (CN)

(72) Inventors: Lijun Liu, Beijing (CN); Jianxin Zhi, Beijing (CN); Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 405 days.

(21) Appl. No.: 15/542,440

(22) PCT Filed: Dec. 31, 2015

(86) PCT No.: PCT/CN2015/100055
§ 371 (c)(1),
(2) Date: Jul. 10, 2017

(87) PCT Pub. No.: WO2016/110219
PCT Pub. Date: Jul. 14, 2016

(65) Prior Publication Data
US 2018/0021539 A1    Jan. 25, 2018

(30) Foreign Application Priority Data
Jan. 9, 2015  (CN) .......................... 2015 1 0012049

(51) Int. Cl.
*A61M 16/16* (2006.01)
*A61M 16/10* (2006.01)
*A61M 16/00* (2006.01)

(52) U.S. Cl.
CPC ........ *A61M 16/162* (2013.01); *A61M 16/109* (2014.02); *A61M 16/00* (2013.01); *A61M 16/167* (2014.02); *A61M 2205/3653* (2013.01)

(58) Field of Classification Search
CPC .............. A61M 16/08; A61M 16/0841; A61M 16/1075; A61M 16/1085; A61M 16/109;
(Continued)

(56) References Cited

U.S. PATENT DOCUMENTS 3,757,082 A    9/1973  Goicdechea
4,051,205 A *  9/1977  Grant ................ A61M 16/1075
                                                 261/70

(Continued)

FOREIGN PATENT DOCUMENTS

CN        1684734 A    10/2005
CN      101780301 A     7/2010
(Continued)

*Primary Examiner* — Annette Dixon
(74) *Attorney, Agent, or Firm* — Bayramoglu Law Offices LLC (57) ABSTRACT

The present disclosure discloses a humidification device, and a humidifier and a ventilator to overcome deficiencies in the prior art such as the heating efficiency of a ventilator being relatively low when the amount of water in a humidification device is adequate. The humidification device comprises a heating area and a liquid conveying device conveying a liquid to the heating area, the liquid conveying device comprising a liquid inlet pipeline, the liquid inlet pipeline extending into the heating area and extending to a bottom of the heating area, and a reserved interval being provided between an outlet of the liquid inlet pipeline and the bottom of the heating area. According to the embodiments of the present disclosure it is ensured that the heating efficiency may be increased and the heating time may be reduced in the case of continuous use.

10 Claims, 4 Drawing Sheets

(58) Field of Classification Search
CPC ............ A61M 16/1095; A61M 16/167; A61M 2005/1623; Y10S 261/65
See application file for complete search history.

(56) References Cited

U.S. PATENT DOCUMENTS

| | | | |
|---|---|---|---|
| 4,225,542 | A | 9/1980 | Wall et al. |
| 7,722,016 | B2 * | 5/2010 | Bradley .............. A61M 16/167 |
| | | | 261/70 |
| 9,446,215 | B2 * | 9/2016 | Steg ...................... A61M 16/16 |
| 2004/0050386 | A1 * | 3/2004 | Levine ................ A61M 16/167 |
| | | | 128/203.16 |
| 2008/0054497 | A1 | 3/2008 | Bradley |
| 2008/0054500 | A1 | 3/2008 | Bradley et al. |
| 2011/0156289 | A1 | 6/2011 | Steg et al. |
| 2012/0012186 | A1 | 1/2012 | Tantra |

FOREIGN PATENT DOCUMENTS

| | | |
|---|---|---|
| CN | 201768248 U | 3/2011 |
| CN | 203898892 U | 10/2014 |
| CN | 203898892 U | 10/2014 |
| CN | 104548298 A | 4/2015 |
| CN | 104548299 A | 4/2015 |
| CN | 104548307 A | 4/2015 |
| CN | 104548308 A | 4/2015 |
| CN | 204446899 U | 7/2015 |
| GB | 1509011 A | 4/1978 |

\* cited by examiner

HUMIDIFICATION DEVICE, HUMIDIFIER AND VENTILATOR

CROSS-REFERENCES TO RELATED APPLICATION

This application is the national phase entry of International Application No. PCT/CN2015/100055, filed on Dec. 31, 2015, which is based upon and claims priority to Chinese Patent Application No. CN201510012049.3, filed on Jan. 9, 2015, the entire contents of which are incorporated herein by reference.

TECHNICAL FIELD

The present disclosure relates to human respiratory regulation technologies, and more particularly, to a humidification device, a humidifier and a ventilator.

BACKGROUND OF THE INVENTION

A humidifier of a ventilator is mainly used for increasing humidity of air conveyed to a patient. The air, for a medical purpose, generally does not contain adequate moisture. If the air is used directly, it may damage or irritate a respiratory tract or an upper respiratory tract of a user. Also, the respiratory tract or the upper respiratory tract of the user may be affected by dry and dense secreta of a bypass patient, which may cause airway constriction and even obstruction. By heating the moisture provided by the humidifier, the water vapor output of the humidifier may be increased.

In humidification devices of the existing humidifiers, basically a water storage area and a heating area are integrated into one cavity. When in use, water sufficient to be consumed for a certain time is added to the humidification device. Moisture is slowly provided to the patient for use through airflow provided when the ventilator works and by heating.

Because water sufficient to be consumed for a certain time needs to be stored in the humidification device, more water needs to be filled in the humidification device at the very start. Consequently, lower heating efficiency and longer heating time may be caused when the ventilator just starts working.

SUMMARY OF THE INVENTION

A technical problem to be solved by the present disclosure is to overcome deficiencies in the prior art such as the heating efficiency of a ventilator being relatively low when the amount of water in a humidification device is adequate.

To solve the above technical problem, embodiments of the present disclosure first provide a humidification device, which comprises a heating area and a liquid conveying device conveying liquid to the heating area. The liquid conveying device comprises a liquid inlet pipeline, the liquid inlet pipeline extends into the heating area and extends to a bottom of the heating area, and a reserved interval is provided between an outlet of the liquid inlet pipeline and the bottom of the heating area.

Preferably, the liquid conveying device further comprises an air outlet pipeline, an inlet of the liquid inlet pipeline is lower than an outlet of the air outlet pipeline, an outlet of the liquid inlet pipeline is lower than an inlet of the air outlet pipeline, and both the outlet of the liquid inlet pipeline and the inlet of the air outlet pipeline extend into the heating area.

Preferably, the liquid conveying device further comprises a suspension seal element arranged in the heating area, and the suspension seal element faces towards the outlet of the liquid inlet pipeline and may block off the outlet of the liquid inlet pipeline under a buoyancy action of the liquid in the heating area.

Preferably, the suspension seal element comprises a base part and a seal part arranged on the base part, and the seal part fits to the outlet of the liquid inlet pipeline.

Preferably, the seal part is at least partially positioned in the outlet of the liquid inlet pipeline.

Preferably, the liquid conveying device further comprises an elastic sealing element arranged in the heating area, and the elastic sealing element faces towards the outlet of the liquid inlet pipeline and may open the outlet of the liquid inlet pipeline under the action of air pressure.

Preferably, the elastic sealing element comprises a sealing plate and an elastic element arranged on a bottom of the sealing plate; a sealing member is arranged on the sealing plate facing towards the outlet of the liquid inlet pipeline, and the sealing member fits to the outlet of the liquid inlet pipeline.

Preferably, the humidification device further comprises a liquid storage area connected to the liquid conveying device, and the inlet of the liquid inlet pipeline is connected to the liquid storage area.

The present disclosure further provides a humidifier, which comprises a heating element and the humidification device as mentioned above, wherein the heating element heats the liquid in the heating area of the humidification device.

The present disclosure further provides a ventilator, which comprises a main machine and the humidifier as mentioned above, wherein the main machine is connected to an air inlet of the heating area, and a pipeline that may be connected to a human body is connected to an air outlet of the heating area.

Compared with the prior art, according to the embodiments of the present disclosure, by providing the reserved interval between the outlet of the liquid inlet pipeline and the bottom of the heating area, the liquid level of the liquid in the heating area does not exceed the outlet of the liquid inlet pipeline, so that the phenomenon of low heating efficiency caused by more water in the heating area can be avoided. Furthermore, the humidification device can implement dynamic water supplementation, so that a constant amount of liquid in the heating area can be ensured, thereby avoiding dry burning.

According to the embodiments of the present disclosure, a liquid supplementing operation for the humidification device may be implemented by replacement or by supplementing liquid to the liquid storage area, so that the humidifier is prevented from being frequently opened or closed in a liquid adding process, and thus the humidifier is used very conveniently and efficiently. Furthermore, the heating element is not exposed in a liquid adding process, so that danger of a patient being scalded may be avoided.

Additional features and advantages of the present disclosure will be set forth in the description which follows, and in part will be apparent from the description, or may be learned by implementing the technical solutions of the present disclosure. The objectives and other advantages of the present disclosure may be implemented and obtained by structures and/or procedures particularly indicated in the specification, the claims and the accompanying drawings.

BRIEF DESCRIPTION OF THE DRAWINGS

The accompanying drawings are provided to further understand the technical solutions of the present disclosure or the prior art, and constitute a part of the description. The accompanying drawings for the embodiments of the present disclosure, together with the embodiments of the present disclosure, are provided to interpret the technical solutions of the present disclosure, rather than limiting the technical solutions of the present disclosure.

DETAILED DESCRIPTION OF THE INVENTION

Implementations of the present disclosure will be explained in detail with reference to the accompanying drawings and the embodiments, whereby it can be fully understood how to solve the technical problem by the technical means according to the present disclosure and achieve the technical effects thereof, and thus the technical solution according to the present disclosure can be implemented. It is to be noted that as long as there is no conflict, the embodiments and all the features mentioned in all the embodiments may be combined together in any manner, and the technical solutions obtained in this manner all fall within the scope of protection of the present disclosure.

It is also found in the process of implementing the present disclosure that when the existing humidification device is started up, the liquid in the whole humidification device needs to be heated, which may cause deficiencies of long heating time and low heating efficiency. Moreover, even though an adequate amount of liquid is stored in the humidification device at the very start, liquid still needs to be supplemented to the humidification device after a certain time of use. When the ventilator is used for a long time, it is necessary to frequently open or close the humidifier to take the humidification device out and then put the humidification device into the humidifier after liquid is supplemented. Furthermore, when the humidification device is taken out to add the liquid, a heating bottom plate at a lower end of the humidifier may be exposed, which may cause that the patient or others are scalded. Therefore, the safety is lower.

Figure 1:
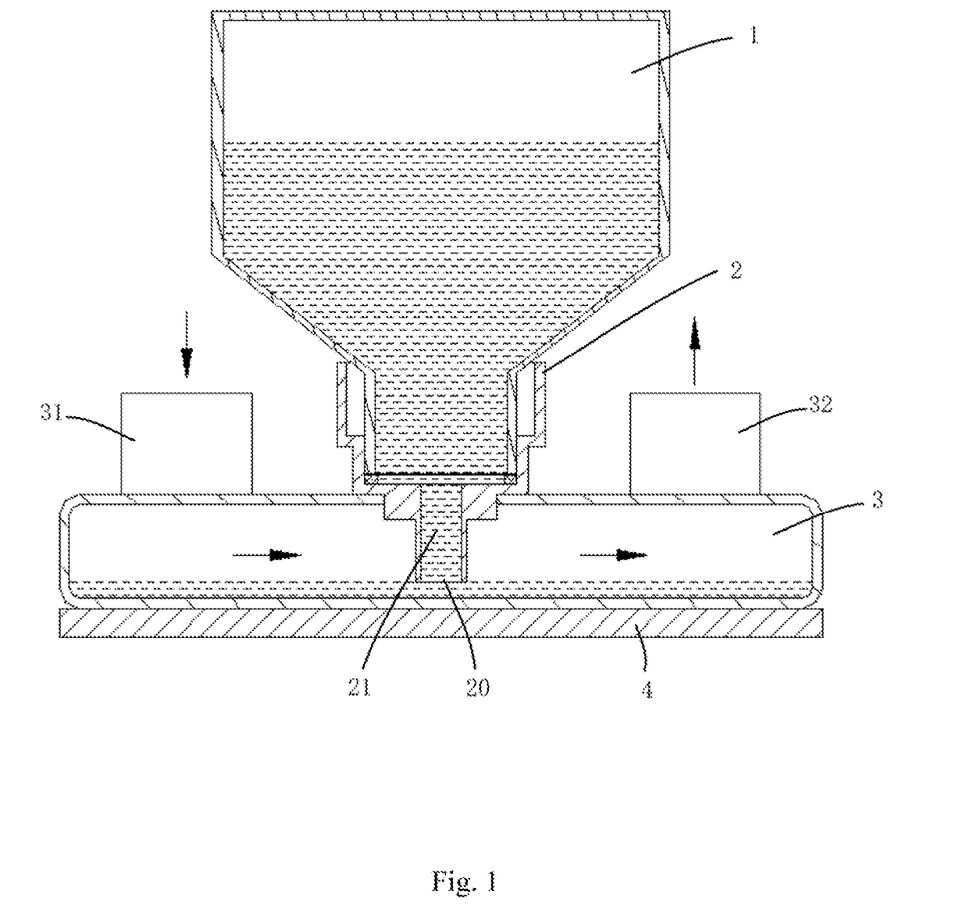
FIG. 1 is a schematic structural diagram of a humidification device according to an embodiment of the present disclosure.

As shown in FIG. 1, the humidification device according to the embodiment of the present disclosure includes a heating area 3 and a liquid conveying device 2 conveying liquid (such as water or aqueous solution) to the heating area 3. The liquid conveying device 2 further may be configured to maintain the liquid in the heating area 3 at a preset volume. The liquid conveying device 2 comprises a liquid inlet pipeline 21, and the liquid inlet pipeline 21 extends into the heating area 3 and extends to a bottom of the heating area 3. A reserved interval is provided between an outlet 20, positioned in the heating area 3, of the liquid inlet pipeline 21 and a bottom of the heating area 3, so that after the liquid enters the heating area 3 from the liquid inlet pipeline 21, the liquid in the liquid inlet pipeline 21 stops flowing into the heating area 3 when a liquid level of the heating area 3 rises above an opening 20 of the liquid inlet pipeline 21 (at least is flush with the outlet 20 of the liquid inlet pipeline 21). The liquid inlet pipeline 21 may be straight or may be bent.

As shown in FIG. 1, the humidification device according to the embodiment of the present disclosure may further comprise a liquid storage area 1. The liquid storage area 1 having an opening may be detachably connected to the liquid conveying device 2, and is communicated with the heating area 3 via the liquid conveying device 2. Preferably, the liquid storage area 1 is connected to the liquid conveying device 2 via the openings oppositely arranged. The opening of the liquid storage area 1 is smaller whereas the opening of the liquid conveying device 2 is larger. When in use, the opening of the liquid storage area 1 is sleeved in the opening of the liquid conveying device 2, and the liquid storage area 1 and the liquid conveying device 2 are connected together through screw thread. Alternatively, the opening of the liquid storage area 1 also may be directly sleeved in the opening of the liquid conveying device 2. As shown in FIG. 1, the opening of the liquid storage area 1 which is filled with water is inserted into the opening of the liquid conveying device 2 by way of inverted insertion.

The reserved interval is provided between the outlet 20, positioned in the heating area 3, of the liquid inlet pipeline 21 and a bottom surface of the heating area 3, so that the liquid inlet pipeline 21 does not contact the heating area 3, and thus the liquid in the liquid conveying device 2 can enter the heating area 3 from the outlet 20 of the liquid inlet pipeline 21 conveniently. Generally, the reserved interval is greater than 5 mm and smaller than 30 mm. The reserved interval is greater than 5 mm, which can allow the liquid in the liquid inlet pipeline 21 to flow out smoothly. The reserved interval is smaller than 30 mm to reduce the amount of liquid in the heating area, so that the liquid in the heating area evaporates more quickly under a heating condition of the same power, and thus the humidification effect is better. Preferably, when the liquid is water, the reserved interval is 10 mm or 15 mm, which may provide the best humidification effect.

In the embodiment as shown in FIG. 1, the outlet 20 of the liquid inlet pipeline 21 is arranged on an end portion of the heating area 3. In other embodiments, the outlet 20 also may be arranged on other portions instead of the end portion, positioned in the heating area 3, of the liquid inlet pipeline 21.

The liquid in the liquid storage area 1 may flow into the heating area 3 via the liquid conveying device 2 under the action of gravity. The heating area 3 is provided with an air inlet 31 and an air outlet 32. The air inlet 31 is configured to guide outside air (air outputted from the ventilator) to enter the heating area 3 for humidification, and the air after being humidified enters, via the air outlet 32, a pipeline connected to a nasal cavity and/or an oral cavity of a user, so that the air is conveyed to the user. Arrows in FIG. 1 indicate an airflow direction indicating that the air enters from the air inlet 31, and flows out from the air outlet 32 via the heating area 3.

When the humidification device according to the embodiment of the present disclosure is applied, the liquid in the liquid storage area 1 enters the heating area 3 via the liquid conveying device 2, and simultaneously, the air in the heating area 3 enters the liquid storage area 1 via the liquid conveying device 2, so that the liquid in the liquid storage area 1 may automatically enter the heating area 3 under the action of gravity. As the liquid in the liquid storage area 1 continuously enters the heating area 3, the liquid level of the heating area 3 may gradually rise. When the liquid level of the heating area 3 rises above the outlet 20 of the liquid inlet pipeline 21, positioned in the heating area 3, of the liquid conveying device 2 (the liquid level of the heating area 3 at least is flush with the outlet 20 of the liquid inlet pipeline 21), the air in the heating area 3 cannot continuously enter the liquid storage area 1 via the liquid conveying device 2, so that the liquid in the liquid storage area 1 cannot be continuously supplemented to the heating area 3, and thus the liquid in the heating area 3 can be maintained at the preset volume. After being heated, the liquid in the heating area 3 is conveyed to the user together with the air via the air outlet 32 so that the liquid in the heating area 3 is consumed, and a gap generated between the liquid level of the heating area 3 and the outlet 20, positioned in the heating area 3, of the liquid conveying device 2 allows the air to enter the liquid conveying device 2 and finally reach to the liquid storage area 1, the liquid in the liquid storage area 1 is supplemented to the heating area 3 continuously under the action of gravity. That is, the liquid in the liquid storage area 1 being supplemented to the heating area 3 is a dynamic balancing process.

An internal space formed by the liquid storage area 1, the liquid conveying device 2 and the heating area 3 is sealed. When there is no liquid in the heating area 3 or the liquid level of the heating area 3 is lower than the outlet 20 of the liquid inlet pipeline 21, the liquid in the liquid storage area 1 enters the heating area 3 via the liquid conveying device 2 under the action of gravity and an atmospheric pressure. When the liquid in the liquid storage area 1 is supplemented to the heating area 3 via the liquid conveying device 2 endlessly so that the liquid level of the heating area 3 gradually rises above the outlet 20 of the liquid inlet pipeline 21 (the liquid level of the heating area 3 at least is flush with the outlet 20 of the liquid inlet pipeline 21), the liquid in the liquid storage area 1 stops flowing into the heating area 3 under the action of the atmospheric pressure and thus the liquid in the heating area 3 is maintained at the preset volume. As the liquid in the heating area 3 is consumed (the liquid enters, via the air outlet 32 together with the air entering the heating area 3, the pipeline connected to the nasal cavity and/or the oral cavity of the user), when the liquid level of the heating area 3 is lower than the outlet 20 of the liquid inlet pipeline 21, the liquid in the liquid storage area 1 is supplemented to the heating area 3 under the action of gravity, till the liquid level of the heating area 3 rises above the outlet 20 of the liquid inlet pipeline 21 or the liquid in the liquid storage area 1 is used up.

In the embodiments of the present disclosure, a sectional area of the outlet 20 of the liquid inlet pipeline 21 may be a circle or an oval, or may be a polygon such as triangle or rectangle, and further may be an irregular shape. To ensure that the liquid conveying device 2 may supplement the liquid to the heating area 3 smoothly in time, the sectional area of the outlet 20 of the liquid inlet pipeline 21 is greater than 7 mm² in some embodiments of the present disclosure.

According to the embodiment as shown in FIG. 1, in the case that the liquid level of the heating area 3 drops or there is no liquid in the heating area 3 at the start, when the liquid in the liquid storage area 1 enters the heating area 3 via the liquid conveying device 2, the air in the heating area 3 needs to enter the liquid storage area 1 from the heating area 3 reversely via the liquid conveying device 2. In this case, the air may enter the liquid storage area 1 upward by way of bubbles, and the liquid in the liquid storage area 1 enters the heating area 3 along with gurgling sound.

Figure 2:
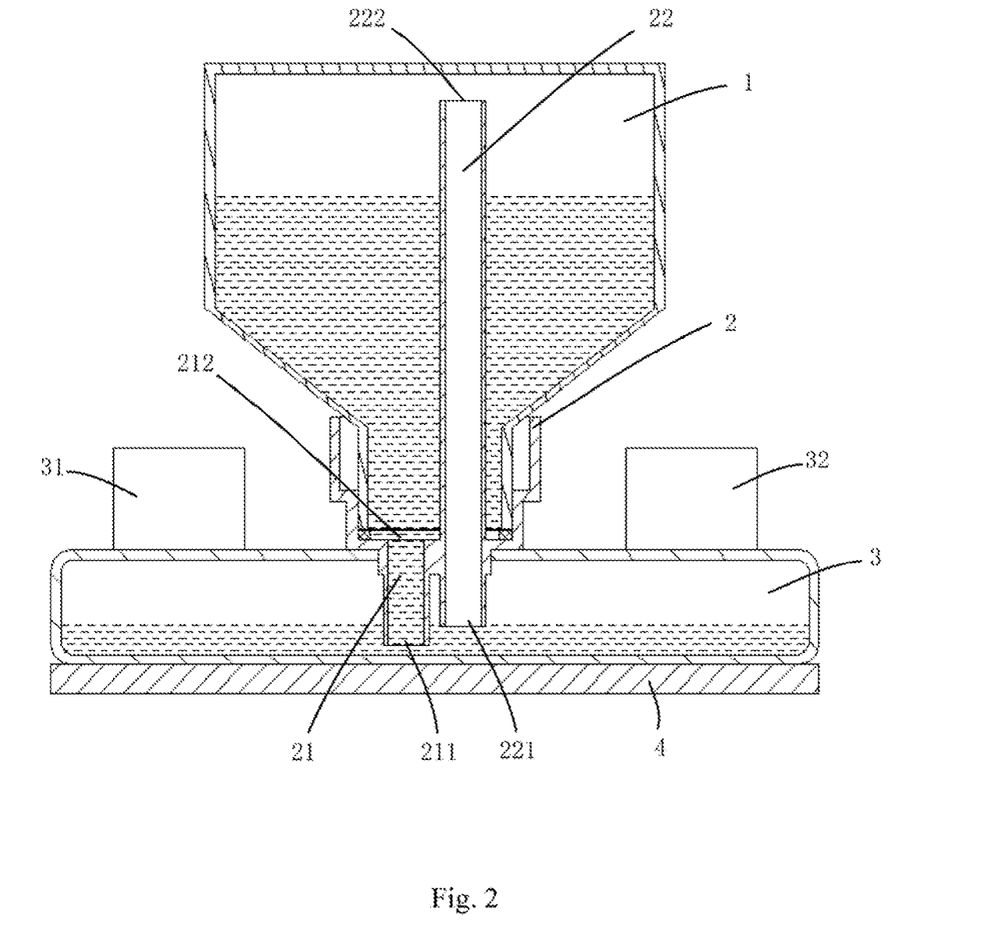
FIG. 2 is a schematic structural diagram of a humidification device according to a second embodiment of the present disclosure.

FIG. 2 illustrates the humidification device according to a second embodiment of the present disclosure. As shown in FIG. 2, the liquid conveying device 2 comprises the liquid inlet pipeline 21 and the air outlet pipeline 22. The liquid inlet pipeline 21 is configured to convey the liquid in the liquid storage area 1 to the heating area 3, and the air outlet pipeline 22 is configured to convey the air in the heating area 3 to the liquid storage area 1. Both an outlet 211 of the liquid inlet pipeline 21 and an inlet 221 of the air outlet pipeline 22 extend into the heating area 3, the inlet 212 of the liquid inlet pipeline 21 is lower than the outlet 222 of the air outlet pipeline 22, the outlet 211 of the liquid inlet pipeline 21 is lower than the inlet 221 of the air outlet pipeline and is closer to a bottom of the heating area 3 than the inlet 221 of the air outlet pipeline. The air outlet pipeline 22 may be straight or may be bent.

When the embodiment as shown in FIG. 2 is applied and when the liquid level of the liquid storage area 1 is lower than the outlet 222 of the air outlet pipeline 22 in the liquid storage area 1, the liquid in the liquid storage area 1 may enter the heating area 3 via the liquid inlet pipeline 21 and the air in the heating area 3 may enter the liquid storage area 1 from the air outlet pipeline 22, so as to keep balance of pressure in the liquid storage area 1 and the heating area 3. When moisture is taken away from the heating area 3 so that the amount of the water in the heating area 3 is reduced and thus the liquid level is lower than the inlet 221 of the air outlet pipeline 22 in the heating area 3, the air in the heating area 3 may enter the liquid storage area 1 via the air outlet pipeline 22, the liquid in the liquid storage area 1 may flow into the heating area 3 via the liquid inlet pipeline 21, and thus the liquid level in the heating area 3 rises above the inlet 221 of the air outlet pipeline 22 (the liquid level of the heating area at least is flush with the inlet 221 of the air outlet pipeline 22). At this moment, the liquid in the liquid storage area 1 stops flowing into the heating area 3, so that the liquid in the heating area 3 is maintained at the preset volume. By virtue of this structure, when the liquid is supplemented to the heating area 3, the liquid is conveyed from the liquid inlet pipeline 21 to the heating area 3 and the air is conveyed from the air outlet pipeline 22 to the liquid storage area 1. Moreover, the outlet 222, positioned in the liquid storage area, of the air outlet pipeline 22 is above the liquid level of the liquid storage area 1. Therefore, the liquid in the liquid storage area 1 does not make the gurgling sound, and thus the use is quieter.

Of course, when there is more liquid in the liquid storage area 1 so that the liquid level of the liquid storage area 1 in a usage state is not lower than the outlet 222 of the air outlet pipeline 22 in the liquid storage area 1, the liquid in the liquid storage area 1 may enter the heating area 3 via the liquid inlet pipeline 21 and the air outlet pipeline 22. In this case, the air in the heating area 3 enters the liquid storage area 1 via the air outlet pipeline 22.

When the liquid level of the heating area 3 rises above the inlet 221 of the air outlet pipeline 222 in the heating area 3, the liquid in the liquid storage area 1 stops flowing into the heating area 3 via the liquid inlet pipeline 21, and thus the liquid in the heating area 3 can be maintained at the preset volume.

Figure 3:
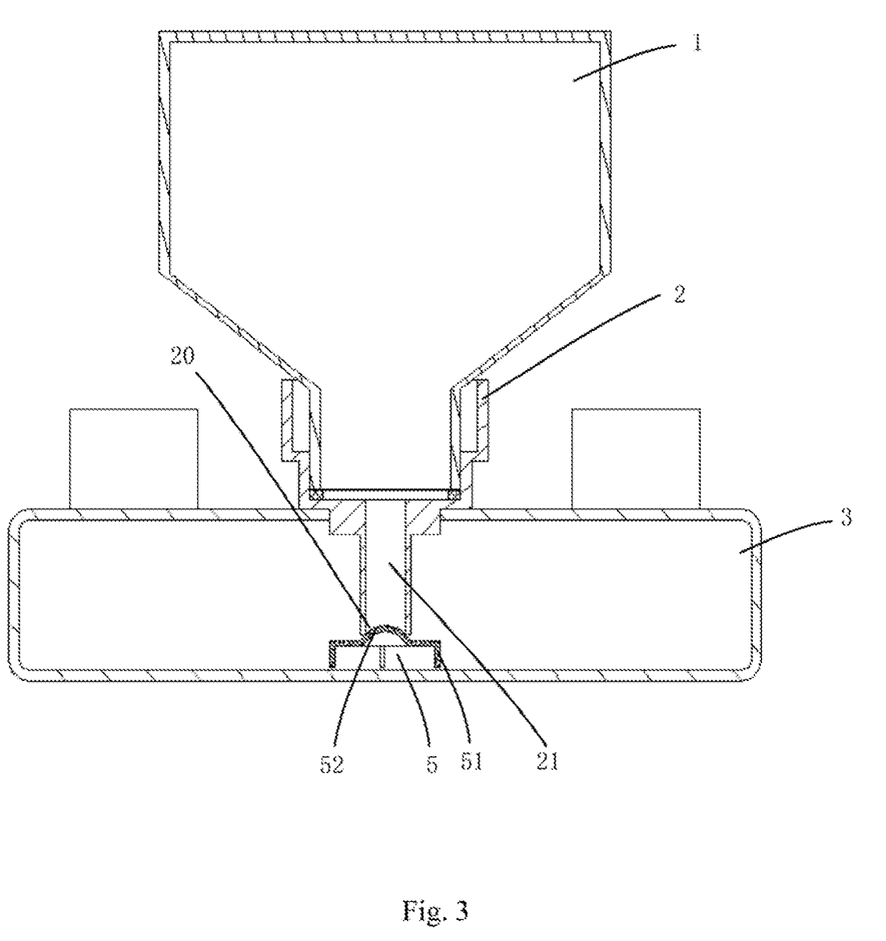
FIG. 3 is a schematic structural diagram of a humidification device according to a third embodiment of the present disclosure.

FIG. 3 illustrates the humidification device according to a third embodiment of the present disclosure. In the embodiment as shown in FIG. 3, a suspension seal element 5, which may block off the outlet 20, positioned in the heating area 3, of the liquid inlet pipeline 21 in the liquid conveying device 2, is arranged in the heating area 3. A density of the suspension seal element 5 is smaller than that of the liquid, and is arranged directly facing the outlet 20 of the liquid inlet pipeline 21.

When there is no liquid in the heating area 3, the suspension seal element 5 contacts the bottom surface of the heating area 3, and is separated from the outlet 20 of the liquid inlet pipeline 21. Consequently, the liquid in the liquid storage area 1 may flow into the heating area 3 via the liquid inlet pipeline 21. As the water continuously enters the heating area 3, the suspension seal element 5 whose density is lower than that of the water liquid gradually rises as the liquid level rises until the outlet 20 of the liquid inlet pipeline 21 is sealed up and thus the liquid in the liquid storage area 1 stops flowing into the heating area 3. When the amount of the liquid in the heating area 3 is gradually reduced, the suspension seal element 5 gradually drops as the liquid level drops. At this moment, the suspension seal element 5 is separated from the outlet 20 of the liquid inlet pipeline 21 again and thus the liquid in the liquid storage area 1 flows into the heating area 3 again.

To guarantee that the suspension seal element 5 can seal the outlet 20 of the liquid inlet pipeline 21 up, a seal structure is arranged on a top, facing towards the liquid storage area 1, of the suspension seal element 5, so as to correspond to the outlet 20 of the liquid inlet pipeline 21.

As shown in FIG. 3, the suspension seal element 5 comprises a base part 51 and a seal part 52 (i.e., the above-mentioned seal structure) on the base part 51. When in use, the seal part 52 is sleeved in the outlet 20 of the liquid inlet pipeline 21, or at least a part of the seal part 52 is sleeved in the outlet 20 of the liquid inlet pipeline 21. An external shape of the seal part 52 fits to an internal shape of the outlet 20 of the liquid inlet pipeline 21. For example, when the outlet 20 of the liquid inlet pipeline 21 is designed as a circular shape, a spherical crown, namely a spherical seal part, is correspondingly arranged on the suspension seal element 5. When the liquid level of the heating area 3 supports the suspension seal element 5 to seal the outlet 20 of the liquid inlet pipeline 21 up, the spherical crown on the suspension seal element 5 precisely blocks off the circular outlet 20 of the liquid inlet pipeline 21.

Preferably, in the embodiment of the present disclosure, an overall height of the suspension seal element 5, namely the sum of the height of the base part 51 and the height of the seal part 52, is greater than a distance from the outlet 20 of the liquid inlet pipeline 21 to the bottom surface of the heating area 3. Moreover, the height of the base part 51 of the suspension seal element 5 is smaller than the distance from the outlet 20 of the liquid inlet pipeline 21 to the bottom surface of the heating area 3. In this way, the seal part 52 is at least partially positioned in the outlet 20 of the liquid inlet pipeline 21, and thus it is ensured that the seal part 52 on the suspension seal element 5 is always positioned in the outlet 20 of the liquid inlet pipeline 21 and is not dropped out. No matter whether there is liquid in the heating area 3 and no matter the liquid level is high or low, the suspension seal element 5 may only have a gap from the liquid inlet pipeline 21 but may not be completely separated from the liquid inlet pipeline 21. Therefore, it is avoided that the outlet 20 of the liquid inlet pipeline 21 cannot be sealed up subsequently when there is liquid in the heating area 3 because the suspension seal element 5 is completely separated from the outlet 20 of the liquid inlet pipeline 21 due to shortage of liquid in the heating area 3.

Figure 4:
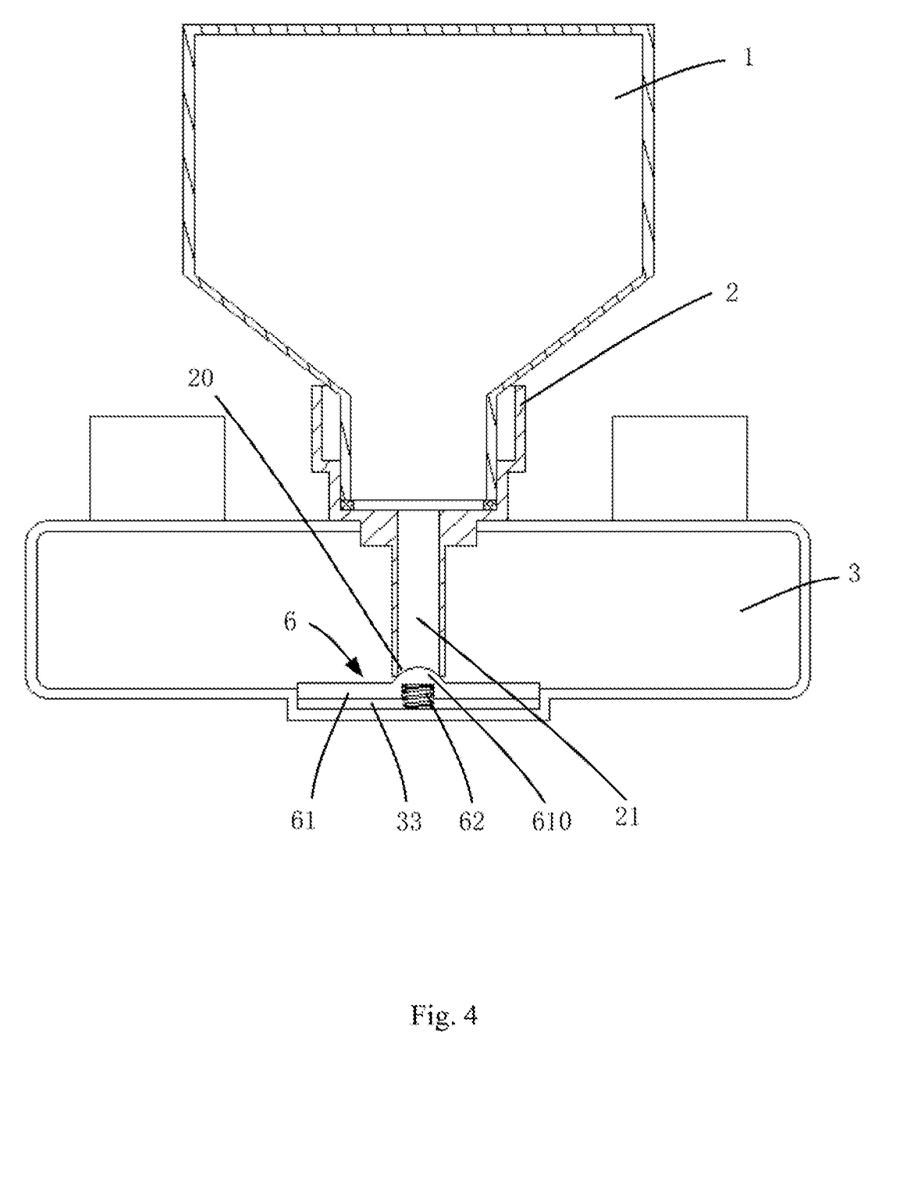
FIG. 4 is a schematic structural diagram of a humidification device according to a fourth embodiment of the present disclosure.

FIG. 4 illustrates the humidification device according to a fourth embodiment of the present disclosure.

As shown in FIG. 4, in the humidification device according to the embodiment of the present disclosure, the heating area 3 is provided with an elastic sealing element 6, which may block off the outlet 29 of the liquid inlet pipeline 21, under the outlet 22 of the liquid inlet pipeline 21 of the liquid conveying device 2. The elastic sealing element 6 comprises a sealing plate 61 and an elastic element 62 arranged at a bottom of the sealing plate. The sealing plate 61 faces towards the outlet 29 of the liquid inlet pipeline 21, and the elastic element 62 props against between the bottom of the sealing plate 61 and the bottom of the heating area 3. The sealing plate 61 is provided with a sealing member 610, and the external shape of the sealing member 610 fits to the internal shape of the outlet 20 of the liquid inlet pipeline 21, so that the sealing member 610 can block off the outlet 20 of the liquid inlet pipeline 21. The elastic element 62 may be, for example, a spring.

The heating area 3 is provided with a cavity 33 corresponding to the elastic sealing element 6. The sealing plate 61 in the elastic sealing element 6 fits to the cavity 33. The elastic element 62 is arranged in the cavity 33. When no air enters the heating area 3, under the action of the spring, the sealing member 610 on the sealing plate 61 props against the outlet 20 of the liquid inlet pipeline 21 to separate the liquid storage area 1 from the heating area 3.

When the ventilator starts to work, the air generated by the ventilator passes through the heating area 3 so that humid air is conveyed to the patient. When the air enters the heating area 3, the air mainly passes from a side, facing towards the outlet 20 of the liquid inlet pipeline 21, of the sealing plate 61, so that the sealing plate 61 is pressed downward, and the spring is stressed and compressed to drive the sealing member 610 on the sealing plate 61 to separate from the outlet 20 of the liquid inlet pipeline 21, and at this moment, the water in the liquid inlet pipeline 21 enters the heating area 3. When the density of the sealing plate 61 is smaller than that of the liquid, as the liquid enters the heating area 3 continuously, the sealing plate 61 gradually rises as the liquid level rises until the outlet 20 of the liquid inlet pipeline 21 is sealed up and thus the liquid in the liquid storage area 1 stops flowing into the heating area 3. When the amount of the liquid in the heating area 3 gradually reduces, the elastic sealing element 6 gradually drops as the liquid level drops. At this moment, the elastic sealing element 6 is separated from the outlet 20 of the liquid inlet pipeline 21 again, and thus the liquid in the liquid storage area 1 starts flowing into the heating area 3 again. When the density of the sealing plate 61 is greater than that of the liquid, and when the liquid level of the heating area 3 is about to rise above the sealing plate 61, under the combined action of a buoyancy force of the liquid and a spring force, the sealing plate 61 may be driven to block off the outlet 20 of the liquid inlet pipeline 21, and thus the liquid in the liquid storage area 1 stops supplementing to the heating area 3.

The humidification device of the humidifier according to the embodiments of the present disclosure is divided into two cavities, namely the liquid storage area and the heating area. The liquid storage area and the heating area are communicated via a liquid conveying device, and the liquid level height of the heating area is controlled by controlling the distance between the outlet of the liquid inlet pipeline in the liquid conveying device and the bottom surface of the heating area. In this way, the total amount of the liquid in the heating area is reduced, and thus the heating efficiency is improved and the heating time is shortened.

According to the embodiment of the humidification device of the present disclosure, by means of the operation of replacing the liquid storage area or taking the liquid storage area down and then adding liquid into the liquid storage area, the liquid adding operation may be implemented, and it is unnecessary to take out the liquid conveying device, the heating area, and the heating element. Therefore, the humidifier is prevented from being frequently opened or closed in the liquid adding process, and thus the humidifier is used conveniently and efficiently. In the operation process of taking the liquid storage area down and then adding liquid into the liquid storage area or directly replacing the liquid storage area, a certain amount of water still may be stored in the heating area to humidify the air, thereby avoiding a phenomenon of dry burning and a danger of the device being overheated due to failure of adding the liquid in time. Furthermore, the heating element is not exposed in the water adding process, so that the danger of the patient being scalded may be avoided.

It is to be noted that in the embodiments of the present disclosure, a dynamic balance may be maintained between the liquid and the air in the liquid storage area 1 and the liquid and the air in the heating area 3 under the control action of intercommunication of the fluid conveying device 2 and fluid (comprising the liquid and the air) flow. As the water in the heating area 3 is gradually consumed, the liquid in the liquid storage area 1 may be continuously supplemented to the heating area 3 until the liquid in the liquid storage area 1 is used up. Of course, before the liquid in the liquid storage area 1 is used up, the user may replace the liquid storage area 1 or take the liquid storage area 1 down and then fill the liquid storage area 1 with the liquid for use again.

In the above embodiment, pressures of the air inlet 31 and the air outlet 32 of the heating area 3 are relatively constant, so that the air pressure in the heating area 3 is relatively constant. In addition, it is to be noted that under a state that the pressures of the air inlet 31 and the air outlet 32 are constant, the liquid storage area 1, the heating area 3 and the liquid conveying device 2 form into a sealing member. A reserved interval is provided between the outlet 20 of the liquid inlet pipeline 21 and the bottom of the heating area 3, so that after the liquid enters the heating area 3 from the liquid inlet pipeline 21, the liquid in the liquid inlet pipeline 21 stops flowing into the heating area 3 when the liquid level of the heating area 3 rises above the opening 20 of the liquid inlet pipeline 21 (at least is flush with the outlet 20 of the liquid inlet pipeline 21).

The humidifier according to the embodiment of the present disclosure comprises a heating element and the humidification device provided in the above embodiments. The heating element is mainly configured to heat the liquid in the heating area 3. As shown in FIG. 1, preferably, the heating element is positioned at the bottom of the heating area 3, so that the water in the heating area 3 may be heated more uniformly. The heating element is configured to generate heat to heat the liquid in the heating area 3. As shown in FIG. 1, in the humidifier according to the embodiment of the present disclosure, the heating element is designed as a heating bottom plate 4 positioned at the bottom of the heating area 3 and directly contacting the bottom of the heating area 3. Correspondingly, the bottom of the heating area 3 has good heat conductivity, and thus may efficiently conduct the heat generated by the heating element to the liquid in the heating area 3. The heating element and the corresponding heating area 3 arranged in such a way may guarantee a higher heating efficiency.

The ventilator according the embodiment of the present disclosure comprises a main machine and the humidifier as mentioned above. The main machine is connected to the air inlet of the heating area. A pipeline connected to a human body is connected to the air outlet of the heating area.

For the humidifier and the ventilator according to the embodiments of the present disclosure, reference is made to the structure and corresponding description of the humidification device and the liquid conveying device of the present disclosure as shown in FIG. 1 to FIG. 4, which are not unnecessarily described herein.

The above are embodiments disclosed by the present disclosure. However, the described contents are merely embodiments adopted for better understanding the technical solutions of the present disclosure rather than limiting the present disclosure. Any person skilled in the art can make any modification and variation to the implementing forms or details without departing from the spirit and scope of the present disclosure. However, the patent protection scope of the present disclosure should still be subjected to the scope defined in the appended claims.

What is claimed is:

1. A humidification device, comprising:
   a heating area and
   a liquid conveying device conveying liquid to the heating area,
   the liquid conveying device comprising a liquid inlet pipeline,
   the liquid inlet pipeline extending into the heating area and extending to a bottom of the heating area,
   a reserved interval being provided between an outlet of the liquid inlet pipeline and the bottom of the heating area,
   wherein the reserved interval is greater than 5 mm and smaller than 30 mm,
   a seal element located in the bottom of the heating area blocks off the outlet of the liquid inlet pipeline under a buoyancy action of the liquid in the heating area,
   the seal element has a base part and a seal part arranged on the base part,
   a sum of a height of the base part and a height of the seal part, is greater than a distance from the outlet of the liquid inlet pipeline to a bottom surface of the heating area, and
   the seal part is always positioned in the outlet of the liquid inlet pipeline.

2. The humidification device according to claim 1, wherein the liquid conveying device further comprises an air outlet pipeline, an inlet of the liquid inlet pipeline is lower than an outlet of the air outlet pipeline, an outlet of the liquid inlet pipeline is lower than an inlet of the air outlet pipeline, and both the outlet of the liquid inlet pipeline and the inlet of the air outlet pipeline extend into the heating area.

3. The humidification device according to claim 2, wherein the outlet of the air outlet pipeline is disposed in a liquid storage area, when the liquid level of the liquid storage area is not lower than the outlet of the air outlet pipeline n the liquid storage area, the liquid in the liquid storage area enters the heating area via the liquid inlet pipeline and the air outlet pipeline, the air in the heating area enters the liquid storage area via the air outlet pipeline; when the liquid level of the heating area rises above the inlet of the air outlet pipeline in the heating area, the liquid in the liquid storage area stops flowing into the heating area via the liquid inlet pipeline.

4. The humidification device according to claim 1, further comprising a liquid storage area connected to the liquid conveying device, wherein the outlet of the liquid inlet pipeline is connected to the liquid storage area.

5. A humidifier, comprising a heating element and a humidification device, wherein the humidification device comprises a heating area and a liquid conveying device conveying liquid to the heating area, the liquid conveying device comprising a liquid inlet pipeline, the liquid inlet pipeline extending into the heating area and extending to a bottom of the heating area, and a reserved interval being provided between an outlet of the liquid inlet pipeline and the bottom of the heating area; and wherein the heating element heats the liquid in the heating area of the humidification device;

wherein the reserved interval is greater than 5 mm and smaller than 30 mm,     a seal element located in the bottom of the heating area blocks off the outlet of the liquid inlet pipeline under a buoyancy action of the liquid in the heating area,     the seal element has a base part and a seal part arranged on the base part,     a sum of a height of the base part and a height of the seal part, is greater than a distance from the outlet of the liquid inlet pipeline to a bottom surface of the heating area, and     the seal part is always positioned in the outlet of the liquid inlet pipeline.

6. The humidifier according to claim 5, wherein the liquid conveying device further comprises an air outlet pipeline, an inlet of the liquid inlet pipeline is lower than an outlet of the air outlet pipeline, an outlet of the liquid inlet pipeline is lower than an inlet of the air outlet pipeline, and both the outlet of the liquid inlet pipeline and the inlet of the air outlet pipeline extend into the heating area.

7. The humidifier according to claim 5, further comprising a liquid storage area connected to the liquid conveying device, wherein the outlet of the liquid inlet pipeline is connected to the liquid storage area.

8. A ventilator, comprising a main machine and a humidifier, wherein the humidifier comprises a heating element and a humidification device, the humidification device comprises a heating area and a liquid conveying device conveying liquid to the heating area, the liquid conveying device comprising a liquid inlet pipeline, the liquid inlet pipeline extending into the heating area and extending to a bottom of the heating area, a reserved interval being provided between an outlet of the liquid inlet pipeline and the bottom of the heating area, and the heating element heats the liquid in the heating area of the humidification device; and wherein the main machine being connected to an air inlet of the heating area, and a pipeline that is capable of being connected to a human body being connected to an air outlet of the heating area;

wherein the reserved interval is greater than 5 mm and smaller than 30 mm,     a seal element located in the bottom of the heating area blocks off the outlet of the liquid inlet pipeline under a buoyancy action of the liquid in the heating area,     the seal element has a base part and a seal part arranged on the base part,     a sum of a height of the base part and a height of the seal part, is greater than a distance from the outlet of the liquid inlet pipeline to a bottom surface of the heating area, and     the seal part is always positioned in the outlet of the liquid inlet pipeline.

9. The ventilator according to claim 8, wherein the liquid conveying device further comprises an air outlet pipeline, an inlet of the liquid inlet pipeline is lower than an outlet of the air outlet pipeline, an outlet of the liquid inlet pipeline is lower than an inlet of the air outlet pipeline, and both the outlet of the liquid inlet pipeline and the inlet of the air outlet pipeline extend into the heating area.

10. The ventilator according to claim 8, further comprising a liquid storage area connected to the liquid conveying device, wherein the outlet of the liquid inlet pipeline is connected to the liquid storage area.

\* \* \* \* \*